United States Patent [19]

Wong et al.

[11] Patent Number: 5,156,850
[45] Date of Patent: Oct. 20, 1992

[54] DOSAGE FORM FOR TIME-VARYING PATTERNS OF DRUG DELIVERY

[75] Inventors: Patrick S. Wong, Palo Alto; Felix Theeuwes, Los Altos; Atul D. Ayer; Anthony L. Kuczynski, both of Palo Alto, all of Calif.

[73] Assignee: ALZA Corporation, Palo Alto, Calif.

[21] Appl. No.: 576,042

[22] Filed: Aug. 31, 1990

[51] Int. Cl.⁵ .............................. A61K 9/24
[52] U.S. Cl. ........................... 424/473; 424/472
[58] Field of Search ......................... 424/472, 473

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,093,709 | 6/1978 | Choi et al. | 424/19 |
| 4,318,400 | 3/1982 | Peery et al. | 128/214 F |
| 4,783,337 | 11/1988 | Wong et al. | 424/468 |
| 4,863,744 | 9/1989 | Urquhart et al. | 424/484 |
| 4,892,739 | 1/1990 | Shah et al. | 424/473 |
| 4,950,486 | 8/1990 | Aya et al. | 424/473 |
| 4,966,769 | 10/1990 | Guttand et al. | 424/473 |
| 4,984,592 | 8/1990 | Ayer et al. | 424/473 |

Primary Examiner—Thurman K. Page
Assistant Examiner—Leon R. Horne
Attorney, Agent, or Firm—Paul L. Sabatine; Edward L. Mandell; Jacqueline S. Larson

[57] ABSTRACT

A dosage form is disclosed that comprises means inside the dosage form for providing a substantially drug-free interval before the dosage form delivers a drug from inside the dosage form. The dosage form in an embodiment comprises a drug on the exterior of the dosage form, which drug is available for immediate delivery.

1 Claim, 6 Drawing Sheets

DOSAGE FORM FOR TIME-VARYING PATTERNS OF DRUG DELIVERY

TECHNICAL FIELD

This invention pertains to a novel dosage form for time-varying patterns of drug delivery. More particularly, the invention concerns a dosage form provided as an osmotic device comprising means for the rate-programmed delivery of a drug in time-varying patterns to a drug recipient.

DESCRIPTION OF BACKGROUND ART

Presently, pharmacy and medicine provide delivery systems for the constant-rate delivery of a drug to a drug-recipient user. The prior art provides infusion pumps as disclosed by Perry, Carpenter and Griesenger in U.S. Pat. No. 4,318,400, oral matrix systems as disclosed by Urguhart and Theeuwes in U.S. Pat. No. 4,863,744, osmotic systems as patented by Theeuwes and Higuchi in U.S. Pat. Nos. 3,845,770 and 3,916,899, osmopolymer-powered systems as provided by Wong, Barclay, Deters and Theeuwes in U.S. Pat. No. 4,783,337, and implants as presented by Choi and Heller in U.S. Pat. No. 4,093,709, for constant-rate delivery of a drug of the longest duration consistent with reproducible therapeutic results.

While these prior art delivery systems provide good therapy and achieve their intended results there are however, some therapeutic programs that require the dose of drug be administered in time-varying patterns of delivery. The time-varying patterns of drug delivery include (1) a drug-free interval followed by drug pulses of various duration for extended periods of time, (2) an immediate drug dose followed by a drug-free interval followed by a drug-delivery period, and (3) a single dose followed by a delayed dose for optimum therapy, and like patterns of drug delivery.

For example, it is known, in *Chronobiologia*, Vol. 13, pages 239 to 243 (1986), that blood pressure has within-day rhythmicity, and that the highest pressure values are seen often in the morning hours just after waking by the patient. The rise in blood pressure occurring at waking requires a dosage form that is administered on retiring and delivers it drug after a drug-free interval during sleep. This drug delivery pattern provides the need for therapy at the appropriate time, thereby substantially lessening the incidence of a waking elevated blood pressure. Presently a dosage form is unavailable to fulfill this need. It is self-evident from the above presentation that a critical and presently unfilled need exists for a delivery system that can delivery a dose of drug in a time-varying pattern of delivery. The need exists for a programmable delivery system that can provide a desired time-profile of drug administration to achieve the intended and therapeutic effect.

DISCLOSURE OF OBJECTS OF THE INVENTION

Accordingly, in the light of the above presentation, it is an immediate object of this invention to provide a novel dosage form that overcomes the shortcomings of the prior art and fully satisfies the critical and unfilled need for the dosage form.

Another primary object of this invention is to provide a dosage form for time-varying patterns of drug delivery for achieving optimum therapy.

Another primary object of this invention is to provide a programmable drug-delivery system that substantially fulfills the pressing need of the prior art and also represents an unexpected improvement in the dispensing art.

Another object of the present invention is to provide a programmable drug-delivery system adapted as a dosage form for a rate-programmed drug delivery at time-varying patterns.

Another object of the present invention is to provide a dosage form comprising structural means for providing drug-free intervals followed by drug-delivery periods of various time durations.

Another object of the present invention is to provide a dosage that can delivery an instant-pulse dose of a therapeutic drug, followed by a delayed delivery of drug, and then deliver a dose of drug.

Another object of the present invention is to provide a dosage form comprising two time spaced-apart doses of drug in a single dosage form.

Another object of the invention is to provide a dosage form comprising two doses of drug in a single dosage form that can be used for twice a day dosing of drug.

Another object of the present invention is to provide a novel dosage form manufactured in the form of a drug delivery device comprising means for delivering a pulsed dose of drug to a human, means for providing a drug-free interval, and then providing a recurring pulse dose of drug to the human.

Another object of the invention is to make available a dosage form that delivers a first or instant dose of drug at bed-time for providing drug during sleep, and a second or delayed drug early in the morning for providing drug therapy on awakening from sleep.

Another object of the invention is to make available a dosage form that delivers a first dose of drug in the morning and a second dose of drug in the afternoon thereby providing two doses of drug therapy from a single dosage form.

Another object of the invention is to provide a dosage form that delivers a drug in pulses to replace twice-a-day dosing of drug or thrice-a-day dosing of drug.

Other objects, features, and advantages of the invention will be more apparent to those versed in the dispensing art from the following specification, taken in conjunction with the drawing figures and the accompanying claims.

BRIEF DISCLOSURE OF THE DRAWING

In the drawing figures, which are not drawn to scale, but are set forth to illustrate various embodiments of the invention, the drawing figures are as follows:

FIG. 2 is a view of the dosage system of FIG. 1, wherein FIG. 2 depicts a dose of drug on the exterior surfaces for administering a drug instantly in a short period of time to a recipient followed by a drug-free interval from the interior of the dosage system;

FIGS, 6, 8 and 10 depict the release rate pattern in hours for delivery systems provided by the invention; and.

Figure 7:
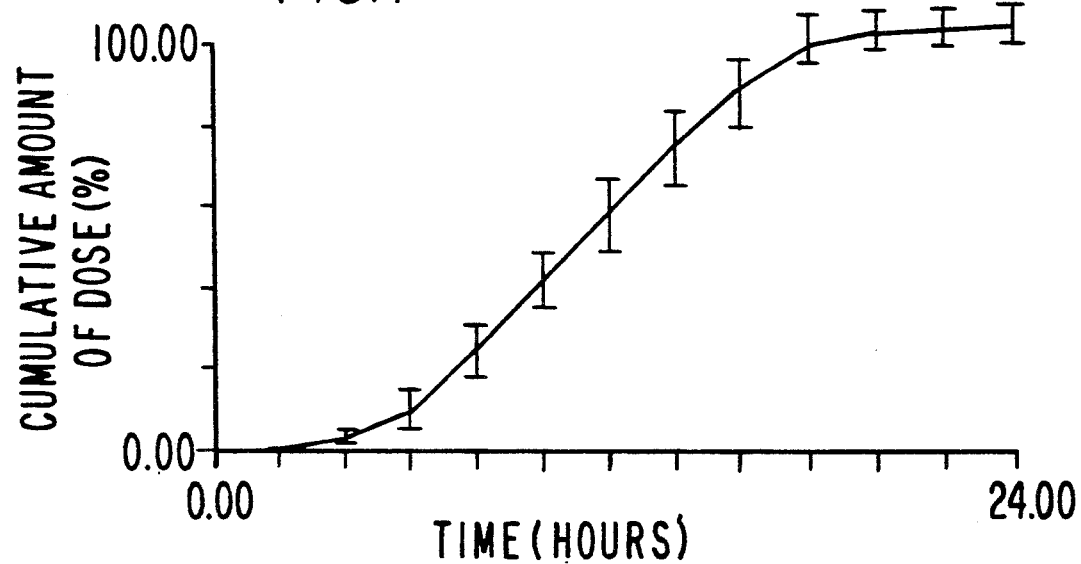
Figure 9:
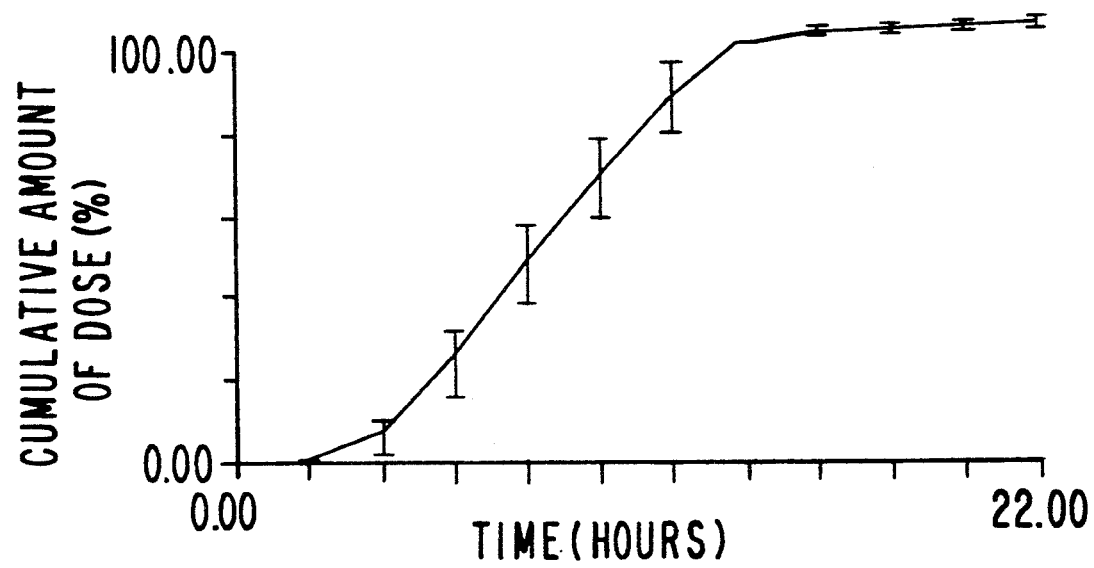
Figure 11:
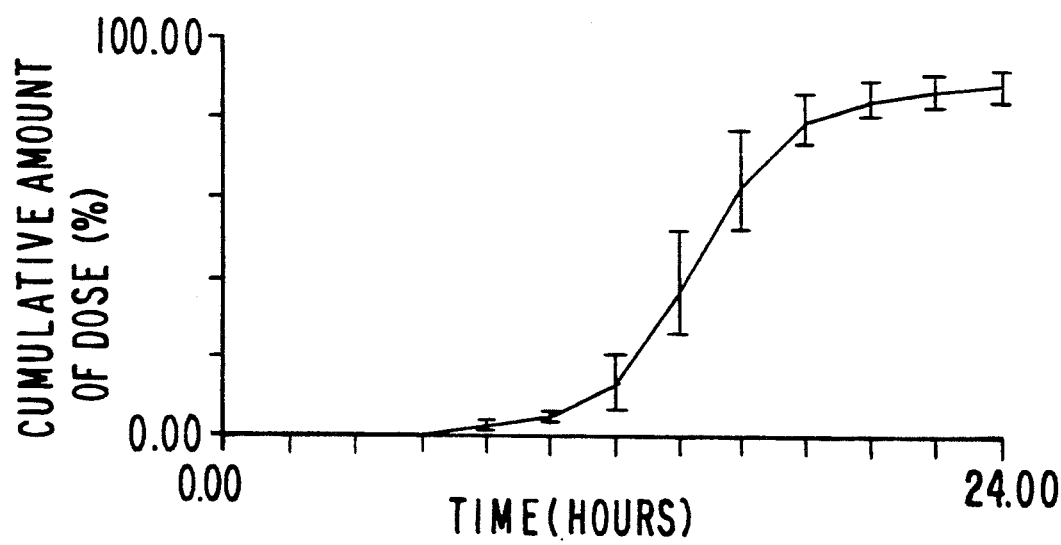

FIGS. 7, 9, and 11 depict the cumulative amount released over a prolonged period of time by dosage forms provided by the invention.

In the drawing figures and in the specification, like parts in related figures are identified by like numbers. The terms appearing earlier in the specification, and in the description of the drawing figures, as well as embodiments thereof, are further described elsewhere in the disclosure.

DETAILED DESCRIPTION OF THE DRAWING FIGURES

Figure 1:
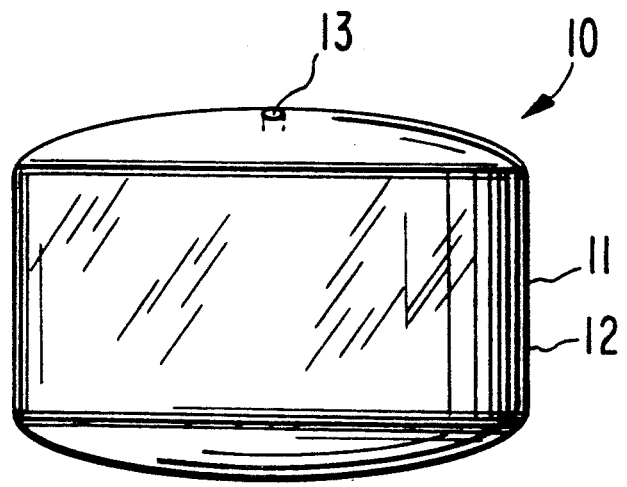
FIG. 1 is a view of a dosage system provided by the invention, which dosage form is designed, sized and adapted for admitting into a biological environment of use for time-varying patterns of drug delivery including drug-free intervals between drug doses.

Turning now to the drawings figures in detail, which drawing figures are an example of the dosage forms provided by the invention, and which examples are not to be construed as limiting, one example of the dosage form is illustrated in FIG. 1 and it is designed by the numeral 10. In FIG. 1, dosage form 10 comprises a body 11 comprising a wall 12 that surrounds and forms an internal compartment, not seen in FIG. 1. Dosage form 10 further comprises at least one exit means 13, or more than one exit means 13 for connecting the interior of dosage form 10 with exterior of dosage form 10.

Figure 2:
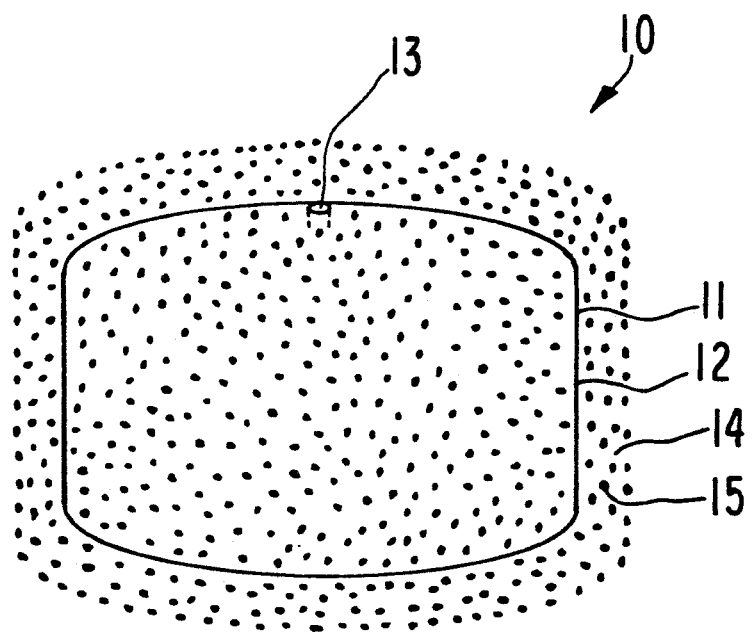

Dosage form 10, as seen in drawing FIG. 2, depicts one presently preferred optional embodiment of the invention, that comprises an external coat 14 on the exterior surface of wall 12. Coat 14 is a composition comprising 1 mg to 200 mg of drug 15, represented by dots. Exterior coat 14 provides instant drug 15 according to the programmable delivery patterns provided by dosage form 10. Drug 15 is blended with an aqueous soluble film-forming carrier such as methyl-cellulose, hydroxypropylcellulose, hydroxypropylmethyl-cellulose, blends of hydroxypropylcellulose and hydroxypropylmethylcellulose, optionally blended with a plasticizer such as polyethylene glycol or acetylated triglycerides or the like. Coat 14 provides instant drug therapy, as film coat 14 dissolves or undergoes dissolution in the presence of fluid and concurrently therewith delivers drug 15 to drug receptor. Coat 14 comprising drug 15 provides (1) instant drug followed by a drug-free interval, and (2) it essentially overcomes the time required for drug 15 to be delivered from the interior of dosage form 10. A start-up time is needed for dosage form 10 to imbibe exterior fluid through wall 12 for dosage form 10 to hydrodynamically dispense drug through exit means 13.

Dosage form 10, as provided by this invention, and as seen in the above drawing figures can be manufactured for administering a drug 15 by the oral route, and in another embodiment, dosage form 10 comprising exterior drug 15 can be sized and shaped for administering drug 15 by the sublingual and buccal routes. The sublingual and buccal routes can be used for quicker therapy and they can be used when a smaller dose of drug is needed for therapy. The buccal and sublingual routes can be used as a by-pass of the first pass of hepatic metabolism of drug 15. The sublingual or buccal routes can be used for administering the first pulse of drug, followed by permitting dosage form 10 to enter the stomach for subsequent drug delivery.

Figure 3:
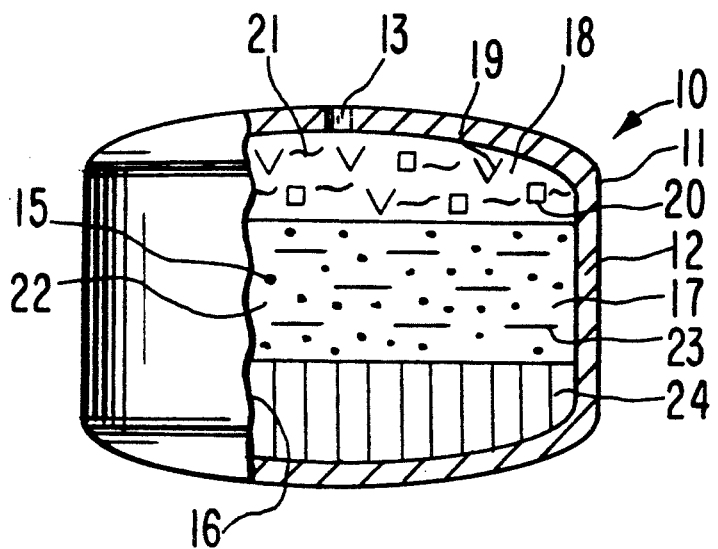
FIG. 3 is an opened view of FIG. 1 for illustrating the internal structure of the dosage system for proving a time-interval, drug-free period followed by a drug delivery period over time.

In drawing FIG. 3, dosage form 10 is manufactured as an osmotic device, and it is seen in opened view at 16. In drawing FIG. 3, dosage form 10 comprises body 11, wall 12, that is sectioned at 16, and which wall 12 surrounds and delivers an internal compartment 17. Wall 12 comprises at least one exit means 13 that connects compartment 17 with the exterior of dosage form 10. Dosage form 10 can comprise more than one exit means 13, as presented later in the specification.

Wall 12 of dosage form 10, comprises totally, or in at least a part, a composition that is permeable to the passage of an exterior fluid present in the environment of use. Wall 12 is substantially impermeable to the passage of drug and other optional ingredients that may be present in compartment 17. The semipermeable wall 12 is substantially insert, that is, it maintains its physical and chemical integrity during the dispensing of a drug from dosage form 10. Wall 12 in a presently preferred embodiment is formed totally or in at least a part of a member selected from the group consisting of a cellulose ether, cellulose ester, cellulose ester-ether. The cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers including cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxy content of 0.5 to 4.7%; cellulose triacylates having a D.S. of 2.9 to 3 such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional semipermeable wall forming polymers include acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable cross-linked selectively permeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); and semipermeable cross-linked poly-(vinylbenzyltrimethyl ammonium chloride). The polymers are known to the art in U.S. Pat. Nos. 3,845,770; 3,916,899; and 4,160,020; and in *Handbook of Common Polymers* by Scott, J. R. and Roff, W. J., 1971, published by CRC Press, Cleveland, Ohio. In another embodiment wall 12 of dosage form 10 of drawing FIG. 3 optionally comprises from 0 weight percent (wt %) to 30 wt % of a member selected from the group consisting of a cellulose ether selected from the group consisting of a hydroxypropylcellulose and a hydroxypropylmethylcellulose, and from 0 wt % to 30 wt % of a poly-ethylene glycol. The total weight of all components comprising wall 12 is equal to 100 wt %.

Dosage form 10 of drawing FIG. 3, comprises a first composition or first layer 18, positioned in compartment 17 next to passageway 13. Layer 18 is drug-free. Layer 18 provides a drug-free period before a drug is delivered from compartment 17, or layer 18 provides a drug-free interval between drug 15 delivered from outside coat 14 and drug delivered from inside compartment 17. First layer 18 comprises a member selected from the group consisting of an osmagent 19, represented by V, and an osmopolymer 20, represented by squares. First layer 18 optionally comprises a binder 21 represented by wavy lines.

The term osmagent 19, as used herein, also includes osmotically effective solute, osmotically effective compounds, and osmotic agent. The osmotically effective compounds that can be used for the purpose of this invention include inorganic and organic compounds that exhibit an osmotic pressure gradient across wall 12 against an external fluid. Osmotically effective compounds useful for the present purpose include magnesium sulfate, magnesium chloride, sodium chloride, lithium chloride, potassium sulfate, sodium carbonate, sodium sulfite, lithium sulfate potassium chloride, calcium bicarbonate, sodium sulfate, calcium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixture thereof. The compound is initially present in first layer 18 in excess and it can be in any physical form such as particle, crystal, pellet, tablet, strip, ground, pulverized, film, or granule. The osmotic pressure of saturated solutions of various osmotically effective compounds and for mixtures of osmotic compounds at 37° C., in water, is listed in Table 1. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure difference is converted into osmotic pressure. In Table 1, osmotic pressures of from 20 ATM to 500 ATM are set forth; of course, the invention includes the use of lower osmotic pressures from zero, and higher osmotic pressures than those set forth by way of example in Table 1. The osmometer used for the present measurements is identified as Model 302B, Vapor Pressure Osmometer, manufactured by the Hewlett Packard Co., Avondale, Pa.

TABLE I

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sucrose | 150 |
| Mannitol-Lactose | 130 |
| Dextrose | 82 |
| Potassium Sulfate | 39 |
| Mannitol | 38 |
| Sodium Phosphate Tribasic - 12H$_2$O | 36 |
| Sodium Phosphate Dibasic - 7H$_2$O | 31 |
| Sodium Phosphate Dibasic - 12H$_2$O | 31 |
| Sodium Phosphate Dibasic - Anhydrous | 29 |
| Sodium Phosphate Monobasic - H$_2$O | 28 |

In another technique, the osmotic pressure is measured using a porous cell impregnated with copper ferrocyanide filled with water and immersed in a vessel containing the aqueous solution. The pressure is measured by means of an attached manometer. The system is allowed to stand until there is no further increase in pressure. Then the osmotic pressure is just balanced by the hydrostatic pressure in the column of solution. A pressure up to several hundred atmospheres can be measured by using a capillary manometer for the pressure measurement. Other methods that can be used for measuring osmotic pressure include using this apparatus and applying a pressure to the solution sufficient to balance an osmotic pressure read in a pressure gauge. Calculations of pressure can e made also from changes in the refractive index of water on compression, and from the application of piezoelectric gauges. The techniques for measuring osmotic pressure are disclosed in *Physical Chemistry* by Walter J. Moore, Third Edition, pages 136 to 137, (1962) published by Prentice-Hall, Inc., Englewood Cliffs, N.J.

For the purpose of this invention, the solubility of osmagent or drug 15 in a fluid can be determined by various art known techniques. One method consists of preparing a saturated solution of means 19 or of drug 15 for example, a fluid plus the means or the drug and ascertaining by analysis the amount of means or drug present in a definite quantity of the fluid. A simple apparatus for this purpose consists of a test tube of medium size fastened upright in a water bath maintained at constant temperature and pressure, for example 37.5° C. and one atmosphere. The fluid and means or drug are placed in the tube and stirred by means of a motor driven rotating glass spiral. After a given period of stirring, a definite weight of the fluid is analyzed and the stirring continued for an additional period of time. If the analysis shows no increase after successive periods of stirring, in the presence of excess solid means or drug in the fluid, the solution is saturated and the results are taken as the solubility of the means or drug in the fluid. Numerous other methods are available for the determination of the solubility of the means or the drug in a fluid. Typical methods used for the measurement of solubility are chemical analysis, measurement of density, refractive index, electrical conductivity, and the like. Details of the various methods for determining solubilities are described in *United States Public Health Service Bulletin, No. 67 of the Hygienic Laboratory; Encyclopedia of Science and Technology,* Vol. 12, pages 542 to 556. 1971, McGraw-Hill, Inc., *"Encyclopaedic Dictionary of Physics,* Vol. 6, pages 545 to 557, 1962, Pergamon Press Inc.; and the like.

The osmopolymers 20 acceptable for forming first layer 18 comprise hydrophilic polymers that are non-cross-linked, or lightly cross-linked, such as with cross-links formed by ionic, hydrogen, or covalent bonds. The osmopolymers 20, for the purpose of this invention, interact with water and aqueous biological fluids and form a solution or a suspension with a high osmotic pressure that are osmotically pumped through exit means 13. The osmopolymers can be of plant and animal origin, prepared by modifying naturally occurring structures, and synthetic polymer osmopolymers. Hydrophilic polymeric materials for the purpose include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water soluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like.

Other osmopolymers include osmopolymers exhibiting a cross-linking of 0.05% to 60%, hydrophilic hydrogels known as Carbopol ®πacidic carboxy polymer, Cyanamer ® polyacrylamides, cross-linked water-swellable indene maleic anhydride polymers, Goodrite ® polyacrylic Aqua-Keeps ® acrylate polymer, diester cross-linked polyglucan, and the like. The osmopolymers are known to the prior art in U.S. Pat. No. 3,865,108 issued to Hartop; in U.S. Pat. No. 4,002,173 issued to Manning; in U.S. Pat. No. 4,207,893 issued to Michaels; and in *Handbook of Common Polymers* by Scott and Roff, published by the Chemical Rubber Company, Cleveland, Ohio.

Other osmopolymers that can be used for providing first layer include agarose, alginates, amylopectin, arabinoglactan, carrageen, eucheuma, fucoidan, furcellaran, gelatin, guar gum, gum agar, gum arabic, gum ghatti, gum karaya, gum tragacanth, hypnea, laminarin, locust beam gum, pectin, polyvinyl alcohol, polyvinyl pyrrolidone, propylene glycol aginates, n-vinyl lactam polysaccharides, xanthan gum, and the like. The osmopolymers are known in *Controlled Release System, Fabrication Technology,* Vol. II, pg 46, (1988), published by CRC Press, Inc.

The osmotic pressure of a hydrophilic polymer, an osmopolymer, or of an osmopolymer osmagent composition, can be measured by those versed in the art by measuring the increase in volume and weight of a composition comprising an osmopolymer, or an osmagent. The measurements are made by placing a composition inside a cup comprising a semipermeable wall that surrounds a salt layer and an inner, fluid impermeable membrane, which has been immersed at 37° C. in water. The osmotic pressure of the composition is determined from the weight gain of the cup compared to a similar cup filled with a saturated solution comprising an osmagent, such as sodium chloride, containing excess osmagent. Since, the osmotic pressure of the osmagent solution is known, the osmotic pressure of the osmopolymer is calculated therefrom.

The osmotic pressure generated from an osmotically active solution can be ascertained by the simplified form of Van't Hoff's Law expressed as by equation 1:

$$\pi = \frac{RTiC_2}{MW_2} \tag{1}$$

wherein $\pi$ is the osmotic pressure generated by an osmotic solute, R is the gas constant, T is the temperature (°K.), $C_2$ is the osmotic solute concentration in solution (mg/ml), $MW_2$ is the molecular weight of the solute, and i is the number of ionizable species or sites per molecule, for small molecules in which the solubility S of the compound can be calculated by substituting C=S, as seen from accompanying equation 2:

$$\pi = \frac{RTiS}{MW_2} \tag{2}$$

For hydrophilic polymers which are usually miscible with water, then, the osmotic potential preferably is measured by water imbibition, in which the weight gain of the polymer is contained inside the semipermeable cup described above. The osmotic pressure of the osmopolymer at any degree of water hydration is calculated from the known water permeability of the semipermeable cup according to equation 3:

$$\pi = \frac{(dv/dt)h}{AK} \tag{3}$$

wherein (dv/dt) is the water imbibition rate, h is the membrane thickness, A is the membrane area, and K is the water permeability of the membrane.

Figure 5:
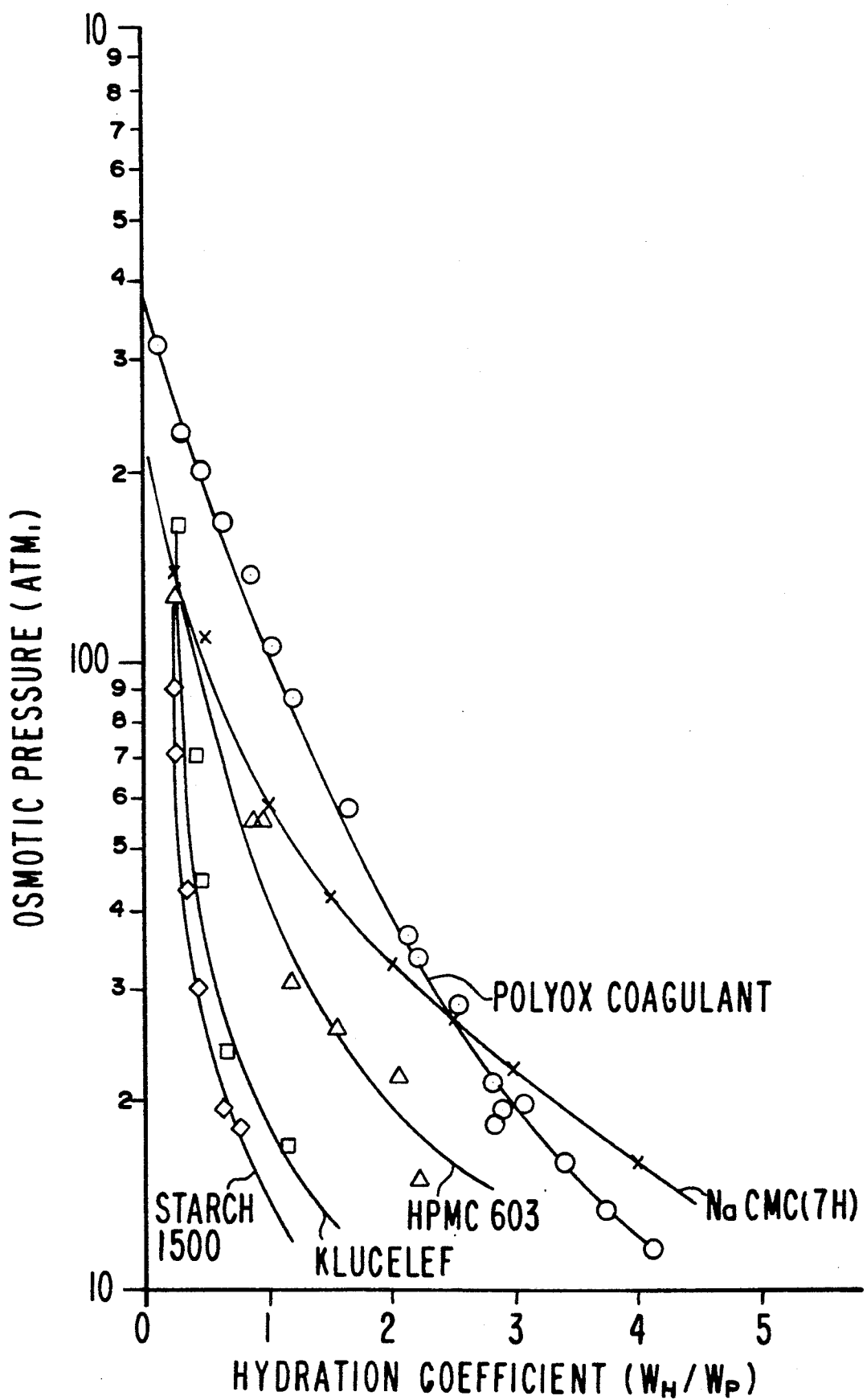
FIG. 5 is a graph that depicts the osmotic pressure in atmospheres developed by a group of osmotic polymers.

Accompanying FIG. 5 shows the osmotic profile for some osmopolymers. The osmotic potential, according to Equation 1, is proportional to the ionizable group in the polymer chain. If one assumes $C_2$ is about the same for all miscible polymers, then the ionizable density ($i/MW_2$) is the determining factor in the osmotic potential for different hydrophilic polymers. In FIG. 5, the line with circles denotes a polyethylene oxide comprising a 5,000,000 molecular weight, the line connected with x indicates sodium carboxymethylcellulose wherein H denotes high viscosity and F denotes food grade cellulose (NaCMC.7HF), the line connected with triangles denotes hydroxypropylmethylcellulose, the line connected with squares denotes hydroxypropylcellulose, and the line connected through diamonds denotes starch. Accompanying Table II compares the $i/MW_2$ values for a group of osmopolymers, depicting that the larger the ionizable density for a polymer, the higher is its osmotic potential which follows the same relative parameters as seen in FIG. 5. In FIG. 5, the hydration coefficient is the ratio ($W_H/W_P$) wherein $W_H$ is the weight of water imbibed into the osmopolymer and $W_P$ is the weight of the dry osmopolymer. In FIG. 5, the word Klucel ® EF denotes hydroxypropylcellulose, the letters HPMC denote hydroxypropylmethylcellulose, and Plyox ® Coagulant denotes polyethylene oxide comprising a 5,000,000 molecular weight.

TABLE II

Physical Chemical Properties of Osmopolymers

| Polymer | i | m. v. of Repeat Unit | ionizable density $i/m.\ v_{-2}\ (\times 10_2)$ |
|---|---|---|---|
| Sorbitol | 6 | 182 | 3.3 |
| Polyethylene oxide | 1 | 44 | 2.27 |
| Sodium carboxyvinylpolymer | 2 | 94 | 2.13 |
| Potassium carboxyvinylpolymer | 2 | 110 | 1.82 |
| Carboxyvinylpolymer | 1 | 72 | 1.39 |
| Pectin | 1 | ~200 | 0.50 |
| Hydroxypropylmethyl cellulose | 1 | 201 | 0.50 |
| Hydroxypropylcellulose | 1 | 336* | 0.30 |

*When Molar Substitution equals 3.0

The first layer 18 generally exhibits a viscosity of about 100 centipoises to 10,000,000 centipoises, when dosage form 10 is in use at an animal temperature of 35° C. to 45° C. For example, first layer 18 can comprise a polyethylene oxide with a molecular weight of 10,000 to 7,000,000, for a 1% solution, the viscosity is generally between 5 to 20,000 centipoises at a room temperature of 23° C.; for a first layer 18 comprising a polyvinyl pyrrolidone with a molecular weight of between 10,000 to 5,000,000, for a 10% solution, the viscosity is generally between 5 to 5000 centipoises at 25° C.; for a hydroxypropylmethylcellulose having a molecular weight of between 9,000 to 241,000, a 2% solution in an aqueous media, the viscosity is about 3 centipoises ubbelohde viscosity at 20° C. to 100,000 centipoises ubbelohde viscosity at 20° C. The viscosity of the first layer, or the viscosity of other compositions is ascertained by conventional measurements. The viscosity, or the resistance that a composition offers to flow when it is subjected to a shear stress can be measured with a Wells-Brookfield Viscometer. Methods on apparatus for measuring viscosity are known in *Pharmaceutical Sciences*, by Remington, 14th Ed., pp. 359–71, (1970), published by Mack Publishing Co., Easton, Pa.

Dosage form 10, as seen in FIG. 3, comprises a second or drug layer 22. Drug layer 22 comprises a drug 15, represented by dots. The term "drug" as used herein, includes any physiologically or pharmacologically active substance that produces a local or systemic effect in animals, including warm blooded mammals; humans and primates; avians; household, sport and farm animals; laboratory animals; fishes; reptiles and zoo animals. The term "physiologically" as used herein, denotes the administration of a drug to produce generally normal levels and functions. The term "pharmacologically", as used herein, denotes generally variations in response to the amount of drug administered to the host. See *Stedman's Medical Dictionary*, 1966, published by Williams and Wilkins, Baltimore, Md.

The active drug 15 that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, anti-Parkinsons, anti-inflammatories, calcium antagonists, anesthetics, antimicrobials, antimalarials, antiparasites, antihypertensives, antihistamines, antipyretics, alpha-adrenergic agonist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, parasympathomimetics, sedatives, sympathomimetics, tranquilizers, urinary tract drugs, vaginal drugs, vitamins, nonsteroidal anti-inflammatory drug, angiotensin converting enzymes, polypeptide drugs, and the like.

Exemplary drugs 15 are very soluble in water and can be delivered by dosage form 10 of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrocyloride, bethanechol chloride, methacholine chloride, pilocarpine hydrochloride, atropine sulfate, scopolamine bromide, isopropamide iodide, trihexethyl chloride, phenformin hydrochloride, methylphenidate hydrochloride, cimetidine hydrochloride, theophylline cholinate, cephalexin hydrochloride, and the like.

Exemplary drug 15 is poorly soluble in water and that can be delivered by dosage form 15 of this invention include diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic, progestational, corticosteroids, hydrocortisone, hydrocorticosterone acetate, cortisone acetate, triamcinolone, methylesterone, 17 beta-estradiol, ethinyl estradiol, ethinyl estradiol 3-methyl ether, prednisolone, 17 beta-hydroxyprogesterone acetate, 19-nor-progesterone, norgestrel, norethindrone, norethisterone, norethiderone, progesterone, norgesterone, norethynodrel, and the like.

Example of other drugs 15 that can be delivered by dosage form 10 include aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chloropromaxine, methyldopa, dihydroxyphenylalanine, pivaloxyethyl ester of alpha-methyldopa hydrochloride, theophylline, calcium gluconate, ketoprofen, ibuprofen, cephalexin, erythromycin, haloperidol, zomepirac, ferrous lactate, vincamine, verapamil, midazolam, diazepam, phenoxybenzamine, diltiazem, milrinone, mandol, guanabenz, hydrochlorothiazide, ranitidine, flurbiprofen, fenbufen, fluprofen, tolmetin, alclofenac, mefenamic, flufenamic, diflunisal, nimodipine, nitredipine, misoldipine, nicardipine, felodipine, lidoflazine, tiapamil, gallopamil, amlodipine, mioflazine, lisinopril, enalapril, captopril, ramipril, endlapriat, famotidine, nizatidine, sucralfate, etintidine, tertatolol, minoxidil, chlordiazepoxide, chlordiazepoxide, hydrochloride, amintriptylin hydrochloride, imipramine hydrochloride, imipramine pamoate, and the like.

The term drug 15, as used for the purpose of this invention also embraces drugs that are administered in the colon to produce a therapeutic effect. The drugs include the drugs conventionally used in the treatment of colitis, ulcerative colitis, Crohn's disease, idiopathic prototis and other disease of the colon. Representative drugs include salicylazosulfapyridine, also known as sulfasalazine, and salazopyrin; adrenocorticosteroids such as hydrocortisone, prednisolone, prednisolone phosphate, prednisolone sulfate, prednisone, perdnisolone metasulphobenzoate sodium, prednisolone sodium phosphate and the like; corticosteroids such as beclomethasone, beclomethasone acetate, beclomethasone valerate, beclomethasone propionate, beclomethasone diproprionate, and the like; cyclosporin; and the like. In another aspect, drug 15 also includes drugs for treatment of irritable bowel syndrome, or drug 15 alters bowl motility and fluid absorption, such drugs are represented by calcium channel blocking drugs, opiads, anticholinergics and benzodiazepides.

Representation of drug 15 also include the non-steroidal anti-inflammatory, analgesic drugs. The non-steroidal anti-inflammatory, analgesic drugs include a member selected from the group consisting of nonsteroidal propionic acid derivatives, nonsteroidal acetic acid derivatives, nonsteroidal fenamic acid derivatives, nonsteroidal biphenylcarboxylic acid derivatives, and nonsteroidal oxicam derivatives. The propionic acid derivatives include a member selected from the group consisting of benoxaprofen, carprofen, flurbiprofen, fenoprofen, fenbufen, ibuprofen, indoprofen, ketoprofen, naproxen, miroprofen, oxaprozin, pranoprofen, pirprofen, suprofen, tiaprofenic acid, fluprofen, alminoprofen, bucloxic acid and the like. The acetic acid derivatives include a member selected from the group consisting of alclofenac acematacin, aspirin, diclofenac, indomethacin, ibufenac, isoxepac, furofenac, fentiazac, clidanac, oxpinac, sulindac, tolmetin, zomepirac, zidometacin, tenclofenac, tiopinac, and the like. The fenamic acid nonsteroid drugs include mefenamic acid, flufenamic acid, niflumic acid, meclofenamic acid, tolfenamic acid, and the like. Representative biphenylcarboxylic carboxylic acid nonsteroid drugs include diflunisal, flufenisal, and the like. Representative nonsteroidal oxicam drugs include isoxicam, piroxicam, sudoxicam, and the like. Other drugs include potassium chloride, potassium carbonate, and the like.

The drug 15 can be in second layer 22 in various forms, such as uncharged molecules, molecular complexes, pharmacologically acceptable salts such as hydrochloride, hydrobromide, sulfate, laurate, palmitate, phosphate, nitrite, borate, acetate, maleate, tartrate, oleate and salicylate. For acidic drugs, salts of metals, amines or organic cations; for example, quaternary ammonium can be used. Derivatives of drugs such as ester, ethers and amides can be used. Also, a drug that is water insoluble can be used in a form that is water soluble derivative thereof to serve as a solute, and on its release from the device, is converted by enzymes, hydrolyzed by body pH or other metabolic processes to the original biologically active form. The amount of beneficial drug 15 in dosage form 10 is generally about from 0.05 ng to 5 g or more, with individual devices continuing, for example, 25 ng, 1 mg, 5 mg, 10 mg, 25 mg, 125 mg, 500 mg, 750 mg, 1.0 g, 1.2 g, 1.5 g, and the like. The dosage form 10 can be administered once, twice or thrice daily. The therapeutically acceptable drugs are known to the art in *Pharmaceutical Sciences,* 14th Ed., edited by Remington, (1979) published by Mack Publishing Co., Easton, Pa., *The Drug, The Nurse, The Patient, Including Current Drug Handbook* by Falconer, et al., (1974–1976) published by Saunder Company, Philadelphia, Pa; *Medicinal Chemistry,* 3rd Ed., Vol. 1 and 2, by Burger, published by Wiley-Interscience, New York; and in *Physician's Desk Reference,* 38 Ed., (1984) published by Medical Economics Co., Oradel, N.J.

Drug 15 is present in second layer 22 with a composition or layer forming ingredient 23, identified by dashes 23. The composition forming ingredients comprise a polymeric carrier selected from the group consisting of a water soluble gum such as carrageenan, fucoidan, gum ghatti, tragacanthin, arabinoglactin, pectin, xanthan, and the like; water soluble salts of polysaccharides such as sodium alginate, sodium tragacanthin, hydroxyalkylcellulose wherein the alkyl member is straight or branched of 1 to 7 carbons such as hydroxymethylcellulose, hydroxyethylcellulose, hydroxypropylcellulose, and the like; synthetic water-soluble cellulose-based layer formers such as methyl cellulose and it hydroxyalkyl methylcellulose derivatives such as a member selected from the group consisting of hydroxyethyl methylcellulose, hydroxypropyl methylcellulose, hydroxybutyl methylcellulose, poloxyethylene comprising a molecular weight of 50,000 to 8,000,000 usually at a polyoxyethylene concentration up to 25 wt %, and the like; and other cellulose polymers such as carboxymethylcellulose.

Second layer 22 can comprise other layer formers such as polyvinyl pyrrolidone, a blend of gelatin and polyvinyl pyrrolidone, glucose, zinc palmitate, aluminum stearate, magnesium oleate, pulverized teflon, halogenated vegetable oil, pulverized talc, and the like. Second layer 22 comprises 0 weight percent to 95 weight percent of a polymeric carrier. Second layer 22 comprises 0 wt % to 5 wt % of a lubricant such as magnesium stearate, corn starch, potato starch, bentonite, citrus pulp, calcium stearate, stearic acid, and the like. Second layer 22 optionally comprises 0 wt % to 15 wt % of a polyethylene glycol as a solubilizing agent and as a lubricant. Second layer 22 optionally comprises from 0 wt % to 20 wt % of an osmagent such as a member selected form the group consisting of magnesium sulfate, magnesium chloride, potassium sulfate, sodium sulfate, sodium chloride, potassium chloride, and the like. The osmagent in second layer 22 imbibes fluid into the layer for enhancing its dispensing from dosage form 10. The amount of all ingredients in second layer 22 is equal to 100 wt %.

Dosage form 10 comprises a third layer 24 or push layer. The push third layer 24 comprises an osmopolymer suitable for forming the third osmotic push layer 24. The third layer comprises an osmopolymer that exhibits fluid imbibition properties. The osmopolymers are swellable, hydrophilic polymers which osmopolymers interact with water and aqueous biological fluids and well or expand to an equilibrium state. The osmopolymers exhibit the ability to swell in water and retain a significant portion of the imbibed water within the polymer structure. The osmopolymers swell or expand to a very high degree, usually exhibiting a 2 to 60 fold volume increase. The osmopolymers can be noncross-linked or cross-linked. The swellable, hydrophilic polymers are in one presently preferred embodiment lightly cross-linked, such cross-links being formed by covalent ionic bonds or residue crystalline regions after swelling. The osmopolymers can be of plant, animal or synthetic origin. The osmopolymers are hydrophilic polymers. Hydrophilic polymers suitable for the present purpose include poly(hydroxy-alkyl methacrylate) having a molecular weight of from 30,000 to 5,000,000; poly(vinyl-pyrrolidone) having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a mixture of hydroxypropyl methylcellulose and sodium carboxymethylcellulose, hydroxypropyl methylcellulose; a water insoluble, water swellable copolymer reduced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams; polyoxyethylene-polyoxypropylene gel; polyoxybutylene-polyethylene block copolymer gel; carbo gum, polyacrylic gel; polyester gel; polyuria gel; polyether gel; polyamide gel; polyamide gel; polypeptide gel; polyamine acid gel; polycellulosic gel; polygum gel; initially drug hydrogels that generally imbibe and absorb water which penetrates the glassy hydrogel and lowers its glass transition temperature; and the like.

Other osmopolymers include polymers that form hydrogels such as Carbopol ® acidic carboxy polymers, a polymer of acrylic acid cross-linked with a polyallyl sucrose, also known as carboxypolymethylene and carboxyvinyl polymer having a molecular weight of 250,000 to 4,000,000; Cyanamer ® polyacrylamides; cross-linked water swellable indene-maleic anhydride polymers; Good-rite ® polyacrylic acid having a molecular weight of 80,000 to 200,000; Polyox ® polyethylene oxide polymers having a molecular weight of 100,000 to 8,500,000 and higher; starch graft copolymers; Aqua-Keeps ® acrylate polymer polysaccharides composed of condensed glucose units such as diester cross-linked polyglucan; and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers,* by Scott and Roff, published by the Chemical Rubber Company, Cleveland, Ohio. The amount of osmopolymer in the third or push osmotic composition is about 0.01 to 99%. In a presently preferred operation arrangement, the osmopolymer composition comprising third layer 24 exhibits a lesser osmotic pressure than the osmotic pressure than second layer 22 and first layer 18. During operation of dosage form 10, fluid is imbibed into dosage form 10 resulting in greater viscosity of third layer 24 than the viscosity of second layer 22 which exhibits a greater viscosity than first layer 18. The present invention provides a sequential osmotic pressure ($\pi$), and (N) viscosity gradient according to equation 4, wherein (1) denotes first layer 18, (2) denotes drug layer 22 and (3) denotes third layer 24.

$$\pi_{(1)} > \pi_{(2)} > \pi > (3)N_{(3)} > N_{(2)} > N_{(1)} \quad (4)$$

The third push layer 24 comprises additionally from 0 wt % to 5 wt % of a lubricant such as magnesium stearate, calcium stearate, potassium stearate, lithium stearate, stearic acid and the like; from 0 wt % to 3 wt % of a colorant such as red ferric oxide; from 0 wt % to 40 wt % of an osmotically effective compound used for the present purpose comprise magnesium sulfate, magnesium chloride, potassium sulfate, sodium sulfate, lithium sulfate, potassium acid phosphate, mannitol, urea, magnesium succinate, tartaric acid, carbohydrates such as raffinose, sucrose, glucose, sodium chloride, and the like; and from 0 wt % to 30 wt % of a binder such as hydroxypropylcellulose, polyvinyl pyrrolidone, polyvinyl alcohol, polyethylene glycol, and the like. The composition of all ingredients present in third layer 24 is equal to 100 wt %.

Figure 4:
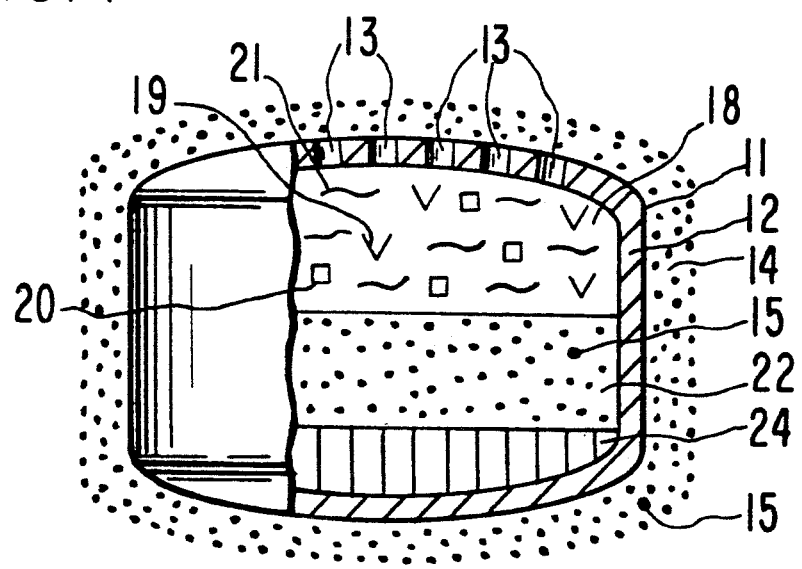
FIG. 4 is an opened view of FIG. 1 depicting a dosage form manufactured as a programmable dosage form that provides time-varying patterns of drug delivery including drug-free intervals between drug doses of various drug-release durations including instant drug delivery and prolonged drug delivery with the latter delivered through a multiplicity of exit passageways.

Dosage form 10, as seen in drawing FIG. 4, comprises at least one passageway 13, or more than one passageway 13. The expansion "at least one passageway" includes aperture, orifice, bore, pore, porous element through which the drug can be pumped, diffuse, travel, or migrate, hollow fiber, capillary tube, porous overlay, porous insert, microporous member, and the like. The expression also includes a material that erodes or is leached from wall 12 in the fluid environment of use to produce at least one passageway in dosage form 10. Representative material suitable for forming at least one passageway, or a multiplicity of passageways, includes an erodible poly(glycolic) acid or poly(lactic) acid member in the wall; a gelatinous filament; poly(vinyl alcohol); leachable materials such as fluid removable pore forming polysaccharides, salts, or oxides, and the like. A passageway or a plurality of passageways can be formed by leaching a material such as sorbitol, sucrose, lactose, fructose or the like, from the wall. The passageway can have any shape such as round, triangular, square, elliptical, and the like, for assisting in the metered release of drug from dosage form 10. Dosage form 10 can be constructed with one or more passageways in spaced apart relation on one or more than a single surface of a dosage form. Passageways and equipment for forming passages are disclosed in U.S. Pat. Nos. 3,845,770 and 3,916,899 by Theeuwes and Higuichi; in U.S. Pat. No. 4,063,064 by Saunders et al; and in U.S. Pat. No. 4,088,864 by Theeuwes et al. Osmotic passageways of controlled drug releasing dimension, sized, shaped and adapted as a drug releasing pore formed by leaching to provide a drug-releasing pore of controlled osmotic release rate are disclosed in U.S. Pat. No. 4,200,098 by Ayer and Theeuwes; and in U.S. Pat. No. 4,285,987 by Ayer and Theeuwes. In drawing FIG. 4, layer 18 is manufactured with increased thickness for increasing the drug-free interval of dosage form 10.

Wall 12 of osmotic dosage form 10 can be formed in one technique using the air suspension procedure. This procedure consists in suspending and tumbling the compressed laminate in a current of air and wall forming composition until a wall is applied to the drug-forming compartment. The air suspension procedure is well-suited for independently forming the wall. The air suspension procedure is described in U.S. Pat. No. 2,799,241; *J. Am. Pharm. Assoc.,* Vol. 48, pp 451 to 459, (1959); and ibid, Vol. 49, pp 82 to 84, (1960). Osmotic dosage forms can also be coated with a wall-forming composition in a Wurster ® air suspension coater, using methylene dichloride-methanol cosolvent, 80:20, wt:wt, or acetone-water cosolvent, 85:15 or 90:10 or 95:5 wt:wt using 2.5 to 5% solids. The Aeromatic ® air suspension coater using a methylene dichloride-methanol cosolvent, 87:13, wt:wt, also can be used for applying the wall. Other wall forming techniques such as pan coating system, wall forming compositions are deposited by successive spraying of the composition on the trilaminate compartment, accompanied by tumbling in a rotating pan. A pan coater is used to produce thicker walls. A larger volume of solvent, such as methanol can be used in a cosolvent to produce a thinner wall. Finally, the wall coated compartments are dried in a forced air oven at 30° C. to 50° C. for up to a week, or a humidity controlled oven at 50 R.H. and 50° C. up to 2 to 5 days, to free the dosage form of solvent. Generally, the walls formed by these techniques have a thickness of 2 to 20 mils with a presently preferred thickness of 4 to 10 mils.

Dosage form 10 of the invention is manufactured by standard manufacturing techniques. For example, in one manufacture the beneficial drug and other ingredients comprising the drug layer facing the exit means are blended and pressed into a solid layer. The drug and other ingredients can be blended also with a solvent and mixed into a solid or semisolid formed by conventional methods such a ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the osmopolymer, hydrogel or push layer, is placed in contact with the drug layer. The osmopolymer layer is manufactured using techniques for providing the drug layer. A delay layer is manufactured using similar procedures. The layering of the drug layer, the osmopolymer layer, and the delay layer, can be fabricated by conventional press-layering techniques. Finally, the three-layer compartment forming members are surrounded and coated with an outer wall. A passageway is laser drilled through the wall to contact the delay layer, with the dosage form optically oriented automatically by the laser equipment for forming the passageway on the preselected surface.

In another manufacture, the dosage form is manufactured by the wet granulation technique. In the wet granulation technique, for example, the drug and the ingredients comprising the drug layer are blended using an organic solvent, such as isopropyl alcohol-ethylene dichloride 80:20 v:v (volume:volume) as the granulation fluid. Other granulating fluid such as denatured alcohol 100% can be used for this purpose. The ingredients forming the drug layer are individually passed through a 40 mesh screen and then thoroughly blended in a mixer. Next, other ingredients comprising the drug layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with a 20 mesh screen. Next, a lubricant is passed through an 80 mexh screen and added to the dry screen granule blend. The granulation is put into milling jars and mixed on a jar mill for 1 to 15 minutes. The delay layer and the push layers are made by the same wet granulation techniques. The compositions are pressed into their individual layers in a Manesty ® press-layer press.

Another manufacturing process that can be used for providing the compartment-forming composition layers comprises blending the powdered ingredients for each layer independently in a fluid bed granulator. After the powdered ingredients are dry blended in the granulator, a granulating fluid, for example, poly(vinyl-pyrrolidone) in water, or in denatured alcohol, or in 95:5 ethyl alcohol/water, or in blends of ethanol and water is sprayed onto the powders. Optionally, the ingredients can be dissolved or suspended in the granulating fluid. The coated powders are then dried in a granulator. This process granulates all the ingredients present therein while adding the granulating fluid. After the granules are dried, a lubricant such as stearic acid or magnesium stearate is added to the granulator. The granules for each separate layer are pressed then in the manner described above.

The osmotic device of the invention is manufactured in another embodiment by mixing a drug with composition forming ingredients and pressing the composition into a solid lamina possessing dimensions that correspond to the internal dimensions of the compartment. In another embodiment the drug and other drug composition-forming ingredients and a solvent are mixed into a solid, or a semisolid, by conventional methods such as ballmilling, calendering, stirring or rollmilling, and then pressed into a preselected lamina forming shape. Next, a lamina of a composition comprising an osmopolymer and an optional osmagent are placed in contact with the lamina comprising the drug lamina. Then, a lamina of a composition comprising a drug-free lamina is placed in contact with the other side of the drug lamina and the three lamina comprising the trilaminate surrounded with a semipermeable wall. The lamination of the middle drug lamina, the first delay lamina and the third lamina comprising the osmopolymer and optional osmagent composition can be accomplished by using a conventional layer tablet press technique. The wall can be applied by molding, spraying or dipping the pressed shapes into wall forming materials. Another and presently preferred technique that can be used for applying the wall is the air suspension coating procedure. The procedure consists in suspending and tumbling the two layered laminate in current of air until the wall forming composition surrounds the laminate. The air suspension procedure is described in U.S. Pat. No. 2,799,241; *J. Am. Pharm. Assoc.,* Vol. 48, pp 451–459 (1979); and, ibid, Vol. 49, pp 82–84 (1960). Other standard manufacturing procedures are described in *Modern Plastics Encyclopedia,* Vol. 46, pp 62–70 (1969); and in *Pharmaceutical Science,* by Remington, 14th Ed., pp 1626–1979, (1970), published by Mack Publishing Co., Easton, Pa.

Exemplary solvents suitable for manufacturing the wall, the laminates and laminae include inert inorganic and organic solvents final laminated wall. The solvents broadly include members selected for the group consisting of aqueous solvents, alcohols, ketones, esters, ethers, aliphatic hydrocarbons, halogenated solvents, cyclaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane ethylene glycol momoethyl ether, ethylene glycol monoethyl acetate, methylene dichloride, ethylene dichloride, propylene dichloride, carbon tetrachloride, chloroform, nitroethane, nitropropane, tetrachloroethan, ethyl ether, isopropyl ether, cyclohexane, cyclo-octane, benzene, toluene, naphtha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and accompanying claims.

EXAMPLE 1

A dosage form adapted, designed and shaped as an osmotic drug delivery system is manufactured as follows: first, 4,000 g of polyethylene oxide having a molecular weight of about 100,000 is mixed with 5,950 g of sorbitol in a Hobart ® mixer at slow speed for 20 minutes. Then, 4 liters of denatured ethanol is slowly added to the above mixer and the mixing continued for an additional 5 minutes to produce a wet granulation. Next, the wet granulation is dried at 31° C. in an oven for 16 hours, and after cooling to room temperature it is passed through a 20 mesh screen. Finally, 50 g of magnesium stearate is added to the granulation and all ingredients are mixed in a roller mill for 1 to 3 minutes, to yield a drug-free composition.

Next, 7,000 g of verapamil HCL, 2,500 g of polyethylene oxide, having a molecular weight of about 5,000,000 and 500 g of polyvinyl pyrrolidone are mixed in a Hobart ® mixer at slow speed for 30 minutes. Then, 3.6 liters of anhydrous ethanol is added slowly to the above mixer and the mixing continued for an additional 4 minutes to yield a wet granulation. Next, the wet granulation is passed through a 7 mesh screen in a Fluid-Air ® mill at 600 rpm, followed by drying the granules at 30° C. in a forced air oven for 18 hours. The dry granules next are passed through a 7 mesh screen in a Fluid-Air ® mill jacketed with chilled water (4° C.) at 550 rpm. Finally, 50 g of magnesium stearate is added to the granulation and all the ingredients mixed in a V-blender for 3 minutes to yield a drug composition.

Next, an osmotic or push composition is prepared by passing separately through a 40 mesh screen the following ingredients: 8,470 g of sodium carboxymethyl cellulose with a molecular weight of 700,000, 940 g of hydroxypropyl cellulose with a molecular weight of 60,000, 470 g of sodium chloride and 100 g of ferric oxide. All of the screened ingredients are then thoroughly mixed in a mixer to yield a homogeneous mix. Then, with continuous mixing, 40 ml of denatured anhydrous ethanol are slowly added and mixing is continued for 2 more minutes to yield a wet granulation. Next, the wet granulation is passed through a 20 mesh screen, dried at room temperature for 16 hours and passed again through a 20 mesh screen. Finally, 20 g of magnesium stearate is added to granulation and the ingredients mixed in a roller mill for 3 minutes to yield an osmotic composition.

A three-layered Manesty tablet press is used for forming the three-layer laminate. The press is set with 7/16" diameter dies and standard concave punches. First, 200 mg of the drug-free composition is added to the die and tamped, then, 380 mg of the second or drug composition is added to the die and tamped, and then, 120 mg of the third or osmotic composition is added to the die and the three laminae are compressed at 3 ton compression pressure to yield the three laminae in contacting laminated arrangement.

Next, the laminates are surrounded with a semipermeable wall. The wall-forming composition comprises 70% cellulose acetate having an acetyl content of 39.8% and 30% hydroxypropylcellulose with a molecular weight of 60,000. The wall-forming composition is dissolved in methylene chloride:methanol (80:20 wt:wt) solvent to make a 4% solids solution. The wall-forming composition is sprayed onto and around the laminates in an Aeromatic Air ® suspension Coater. Finally, the coated laminates are dried for 48 hours in a humidity oven set at 50% relative humidity and 50° C. to evaporate the coating solvents. The coated wall surrounding the laminate weighed 28 mg.

Figure 6:
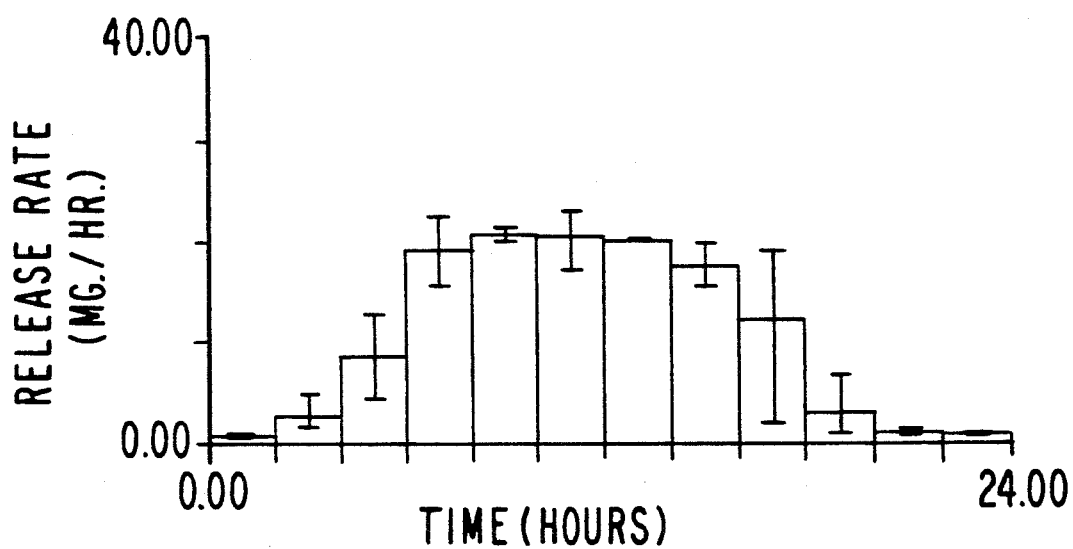

Next, two 40 mil exit ports are drilled on the drug-free or delay-layer side of the dosage form. Accompanying FIG. 6 depicts the release rate over time and FIG. 7 depicts the cumulative amount of drug released release after a drug-free interval.

EXAMPLE 2

Figure 8:
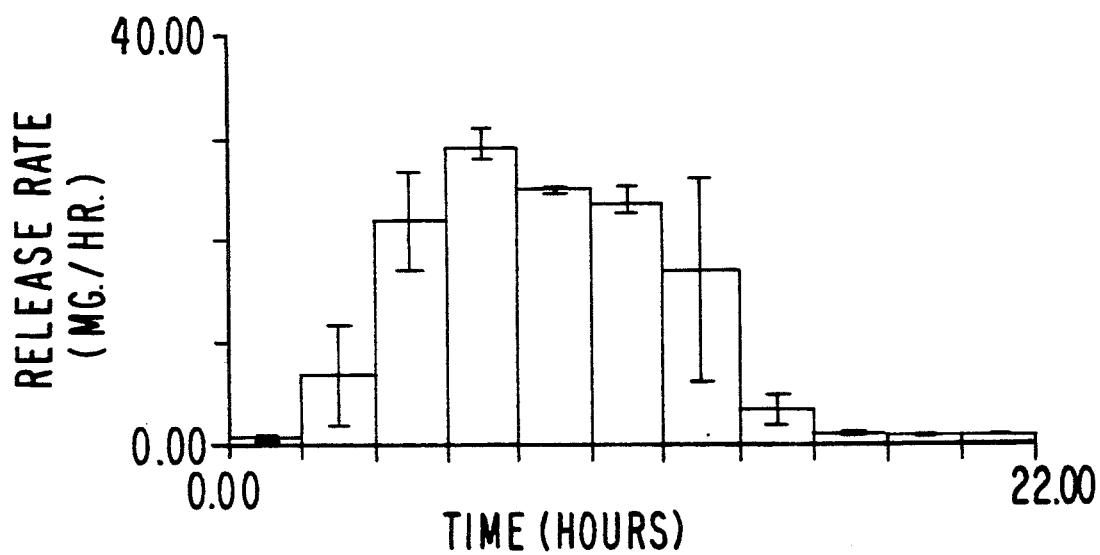

Following the procedure of Example 1, an osmotic device is manufactured comprising a first or drug-free composition consisting of 92% sorbitol; 2.5% polyethylene oxide exhibiting a 5,000,000 molecular weight; 4% polyvinyl pyrrolidone; and 1.5% magnesium stearate. Accompanying FIG. 8 depicts the release rate of the drug verapamil HCl over time and accompanying FIG. 9 depicts the cumulative amount of drug released after a drug-free period.

EXAMPLE 3

Figure 10:
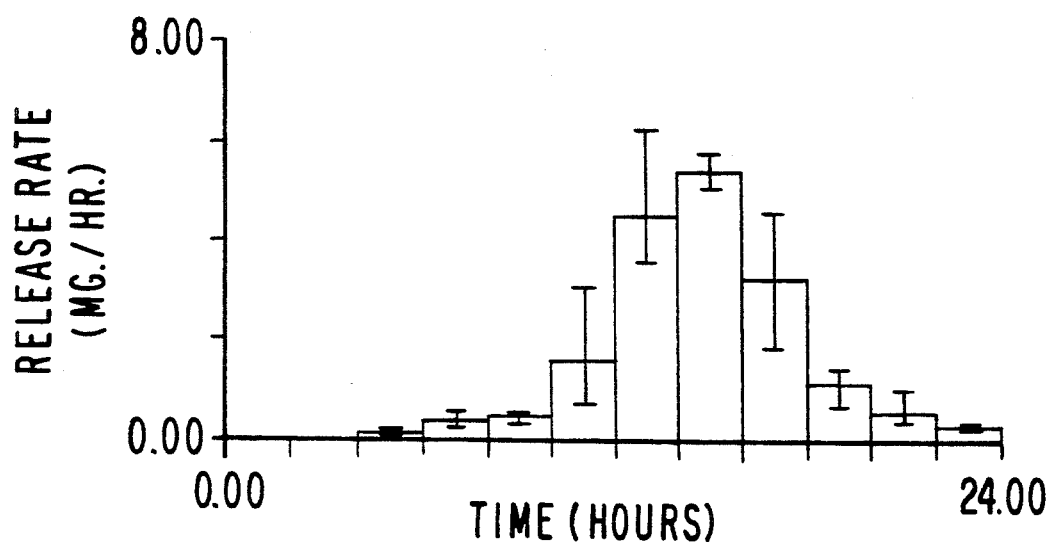

Following the procedure of EXAMPLE 1, an osmotic device is manufactured with a drug composition comprising: 40% nicardipine; 58.5% polyethylene oxide having a molecular weight of 300,000; 1% polyvinyl pyrrolidone; and 0.5% magnesium stearate. Following the procedure, the final osmotic device comprised a first drug-free layer weighting 250 mg, a second or drug layer weighing 100 mg, and a third osmotic layer weighing 250 mg. The wall of the osmotic device comprises 95% cellulose acetate having a 39.8% acetyl content and 5% polyethylene glycol having a 4,000 molecular weight, and a 3 mil thickness. Accompanying FIG. 10 depicts from the osmotic device the release rate of nicardipine over time and FIG. 11 depicts the cumulative amount of drug release following a drug-free period.

EXAMPLE 4

An osmotic delivery device manufactured in the appearance of an osmotic tablet shaped, sized and adapted for oral admittance into the gastrointestinal tract is made as follows: first, a drug-free composition is prepared by screening through a 40 mesh screening 205 g of polyethylene oxide having a 150,000 molecular weight, and screening through a 40 mesh screen 315 g of mannitol and fructose followed by blending the two ingredients in a blender, for 15 minutes. Next, 200 ml of ethanol is added to the blender and the mixing continued for 5 minutes, to yield a wet granulation. The wet granulation next is dried at 37° C. in an air oven for 12 hours, and the dried granulation passed through a 20 mesh screen. Finally, 5 g of stearic acid is added to the granulation and all the ingredients thoroughly blended in a roller mill for 4 minutes, to yield a drug-free composition.

Next, a drug composition is prepared as follows: first, 105 of polyethylene oxide having an approximate molecular weight of 300,000 is screened through a 40 mesh stainless steel screen, then 200 of diltiazen HCL is screened through the 40 mesh screen, next 25 g of hydroxypropylcellulose is passed through the screen, 2 g of potassium chloride is passed through the 40 mesh screen and finally 5 g of sorbitol is passed through the 40 mesh screen. Next, all the screened ingredients are added to the bowl of a blender and the ingredients dry blended for 15 to 20 minutes to produce a homogeneous blend. Then, a granulation fluid is prepared comprising 250 ml of ethanol and 250 ml of isopropyl alcohol, and the granulating fluid added to the blending bowl; first, 50 ml of the granulation fluid is sprayed into the bowl with constant blending, then 1000 ml of the granulation fluid is added slowly to the bowl and the wet mass blended for another 15 to 20 minutes. Then, the wet granules are passed through a 16 mesh screen and dried at room temperature for 24 hours. Next, 10 g of calcium stearate is added to the dry granules, and all the ingredients roll mixed for 20 to 30 minutes on a standard two-roll mill.

Next, a third or osmotic composition is prepared as follows: first, 170 g of poly(ethylene oxide) having a molecular weight of 5,000,000 is screened through a 40 mesh screen, then 10 g of sodium chloride, is passed through the 40 mesh screen, and the ingredients added to a mixing bowl and blended for 10 to 15 minutes. Then, a granulation fluid is prepared by mixing 350 ml of ethanol and 150 ml of isopropyl alcohol, and the granulation fluid added to the blending bowl in two steps. First, 50 ml of the granulation fluid is sprayed into the bowl with constant blending; then 110 ml of the granulation fluid is slowly added to the bowl and the wet blend mixed for 15 to 20 minutes to a homogeneous blend. Then, the wet blend is passed through a 16 mesh screen, spread on a stainless steel tray and dried at room temperature of 22.5° C. for 24 hours. The dried blend is passed through a 16 mesh screen, then roll milled with 2 g of magnesium stearate on a two-roll mill for 20 to 30 minutes.

A number of three-layer dry cores are prepared by pressing the three compositions on a Manesty three-layer press. The drug-free composition is fed into the cavity mold of the press and compressed into a solid layer, then, the drug composition is fed into the cavity mold of the press and compressed into a solid layer, then the third or osmotic composition is fed into the cavity overlaying the compressed two layers and pressed into a solid layer to form a three-layered drug core.

The drug cores next are coated with a semipermeable wall forming composition comprising 35 g of cellulose acetate having an acetyl content of 39.8%, 25 g of cellulose acetate having a 32% acetyl content, and 10 g of hydroxypropyl-cellulose, having a molecular weight of 200,000 in a solvent comprising 1960 ml of methylene chloride and 820 ml of methanol. The drug cores are coated with the semipermeable wall forming composition until the wall surrounds the drug core. A Wurster ® air suspension coater is used to form the semipermeable wall. The coated cores are then spread on a tray and the solvent evaporated in a circulating air oven at 50° C. for 65 hours. After cooling to room temperature, three 0.85 mm diameter passageways are laser drilled through the semipermeable wall connecting the exterior of the osmotic device with the drug-free composition. The dosage form, after a drug-free interval delivers drug for and extended period.

EXAMPLE 5

An osmotic dosage form is prepared according to Example 4 for administering after a delayed interval a therapeutically effective amount of a member selected from the group consisting of a nimodipine, nitredipine, nisoldipine, felodipine, lidoflazine, trapemil, isradipine, gallopamil, amlodipine, mioflazine, nilvadipine, and caroverine.

EXAMPLE 6

An osmotic device form is prepared according to claim 4 for the delayed administration of a therapeutically effective amount of a vasodilator selected from the group consisting of amyl nitrate, glyceryl trinitrate, octyl nitrite, sodium nitrite, erythrityl tetranitrate, isosorbide dinitrate, mannitol hexanitrate, pentaerythritol tetranitrate, pentritol, triethanolamine trianitrate, and trolnitrate phosphate.

EXAMPLE 7

A dosage form sized, shaped and adapted as an osmotic device for oral administration into the gastrointestinal tract of a human is made as follows: first, a drug-free composition is prepared by individually screening through a 40 mesh screen potassium chloride crystals, mannitol, cross-linked polyvinyl pyrrolidone and calcium stearate. The potassium chloride crystals were dried in an oven for 4 hours at 50° C. prior to the granulation to remove moisture. Next, noncross-linked polyvinyl pyrrolidone was dissolved in denatured alcohol to prepare a binder solution. The composition forming excipients were mixed next in a standard Hobart ® mixer to produce a consistent wet mixture. The wet mass of wet granules were passed through a 16 mesh screen, spread on a flat pan and dried in a 50° C. forced air ambient humidity for approximately 24 hours to remove the granulation ethanol solvent. The dried granules were passed through a 16 mesh screen, and blended with calcium stearate in a blender for 2 minutes to yield a drug-free composition.

A drug composition comprising guanabenz acetate for the treatment of hypertension is prepared by screening it through a 60 mesh screen, followed by screening microcrystalline cellulose, polyvinyl pyrrolidone and mannitol independently through a 40 mesh screen. Next, all the ingredients are blended for about 20 minutes to produce a homogeneous blend. Next, silicon dioxide is screened through an 80 mesh screen, and then magnesium stearate is screened through the 80 mesh screen. The screened silicon dioxide and magnesium stearate are added to the blend and all the ingredients blended for 5 minutes.

Next, a push layer comprising phenylene oxide having a 5,000,000 molecular weight, hydroxypropylmethylcellulose, ferric oxide and ethyl alcohol are blended to a wet granulation. The wet granulation is screened through a 16 mesh screen and dried in at 50° C. in an oven overnight. The dried granules are screened through a 16 mesh screen. Then, magnesium stearate is screened and added to the dried granulation. Finally, all the ingredients are blended for 5 minutes to yield a homogeneous blend.

The dosage form comprising the first drug-free layer, the drug layer and the push layer is prepared in a Carver ® press using a ¼ inch, standard concave die. First, the drug-free layer is placed in the die and pinched to compress the granulation. Next, the middle-forming drug layer is placed on top of the drug-free layer and compressed to form a continuous middle layer. Then, the third-forming layer is placed on top of the middle layer and compressed with a force of 2.5 tons of force.

The three-layer laminate is surrounded with a wall in an Aeromatic ® Coater. The wall-forming composition comprises 51 of cellulose acetate having an acetyl content of 43.5%, 9 g of hydroxypropylcellulose and a cosolvent containing 1,170 ml of methylene chloride and 490 ml of methanol. During the wall-forming process, 960 ml of wall-forming solution is used to apply a 12.3 mg wall on each three-layered dosage form. The dosage forms are dried in an oven overnight at 50° C. to yield a final dry wall of 10.4 mg per dosage form. A single 15 mil (0.325 mm) passageway is drilled through the wall connecting the exterior of the dosage form with the first layer. In an automatic laser drilling technique, the first layer is selected by photo examination apparatus of the layer. The dosage form comprises 4 mg of guanabenz acetate.

Next, an exterior, quick-releasing guanabenz acetate lamina and other exterior forming lamina ingredients comprising hydroxypropyl-cellulose, polyethylene oxide and a small portion of hydroxypropyl-methylcellulose are added and blended in a moving current of air containing distilled water and magnesium stearate, to yield an immediate release layer that is compressed around the dosage form. Finally, the lamina wall coated compartments are dried to yield the final dosage form. The exterior immediate release layer comprises 4 mg of guanabenz acetate. The dosage form provided by this example is indicated for twice a day (b.i.d.) therapy. The dosage form on entering the gastrointestinal tract delivers the guanabenz acetate immediately, the first dose, and several hours later commences to delivery the guanabenz acetate, the second dose. The immediate first dose provides antihypertensive action that reaches a therapeutic peak followed by a drug-free interval and then the second dose that provides antihypertensive action that reaches its therapeutic peak to enable the blood pressure to approach baseline values. The dosage form accordingly provides a favorable therapeutic index, with convenient, as a compliance-enhancing b.i.d. dosage form.

DESCRIPTION OF METHOD OF PERFORMING THE INVENTION

A presently preferred embodiment of the invention pertains to a method for delaying the delivery of a drug to the gastrointestinal tract of a human followed by delivery of a drug at a controlled rate and continuously, which method comprises the steps of: (A) admitting orally into the human's gastrointestinal tract a dispensing device comprising: (1) a wall comprising means for imbibing an external aqueous fluid through the wall into the dispensing device, which wall surrounds and forms an internal compartment; (2) a first composition in the compartment, said compartment comprising a drug-free composition for delaying the delivery of the drug from inside the dispensing device for up to 6½ hours from the compartment; (3) a second composition in the compartment comprising a dosage unit amount of drug; (4) a third compartment in the compartment for pushing the drug from the compartment; (5) exit means in the wall for delivering the drug from the device; (B) imbibing fluid through the wall into the compartment for causing the first composition to be delivered and concomitantly delay the delivery of drug from the compartment; (C) imbibing fluid into the third composition to expand and push the drug from the device; and (D) delivering the beneficial drug from the compartment by the third composition expanding continuously thereby causing the drug to be dispensed through the exit means at a therapeutically effective amount at a controlled rate over a period of time to the human. The dispensing device, in an embodiment of the invention comprises an instant release exterior dosage amount of drug for providing b.i.d. drug delivery.

Inasmuch as the foregoing specification comprises preferred embodiments of the invention, it is understood that variations and modifications may be made herein, in accordance with the inventive principles disclosed, without departing from the scope of the invention.

We claim:

1. A method for administering a dose of a drug twice a day from a single dosage form to the gastrointestinal tract of a warm-blooded animal, which method comprises:
   (a) admitting the dosage form into the gastrointestinal tract of the warm-blooded animal, said dosage form comprising:
   (1) a compartment comprising a drug selected from the group consisting of verapamil, nimodipine, nitredipine, nisoldipine, nicardipine, felodipine, diltiazen, lidoflazine, tiapamil, guanabenz, isradipine, gallopamil, amlodipine, mioflazine, caroverene, diltiazem hydrochloride, and midazolam;
   (2) a wall that surrounds and forms the compartment, said wall comprising a composition that is permeable to the passage of fluid;
   (3) a first composition in the compartment comprising a viscosity of 100 centipoises to 10,000,000 centipoises and a polymer comprising a 9,000 to 10,000,000 molecular weight, said first composition drug-free for producing a drug-free interval prior to the administration of drug from the compartment;
   (4) a second composition in the compartment comprising a drug selected from (1), in a dose amount of the drug for producing a therapeutic effect;
   (5) a third composition in the compartment that expands in the presence of fluid that enters the device;
   (6) exit means in the wall for connecting the exterior of the dosage form with the compartment; and
   (7) a substantially immediate release dose amount of a drug selected from (1), on the exterior surface of the wall;
   (b) administering a dose of drug from the exterior wall by contacting the drug with gastrointestinal fluid;
   (c) imbibing fluid into the compartment thereby causing the third composition to expand and push against the second composition; and
   (d) administering the dose of drug from the drug composition after the first drug-free composition is released from the compartment.

* * * * *